United States Patent [19]

Tøpholm

[11] Patent Number: 5,202,927
[45] Date of Patent: Apr. 13, 1993

[54] REMOTE-CONTROLLABLE, PROGRAMMABLE, HEARING AID SYSTEM

[75] Inventor: Jan Tøpholm, Holte, Denmark

[73] Assignee: Tøpholm & Westermann ApS, Vaerloese, Denmark

[21] Appl. No.: 688,510

[22] PCT Filed: Jan. 8, 1990

[86] PCT No.: PCT/EP90/00031

§ 371 Date: May 30, 1991

§ 102(e) Date: May 30, 1991

[87] PCT Pub. No.: WO90/08448

PCT Pub. Date: Jul. 26, 1990

[30] Foreign Application Priority Data

Jan. 11, 1989 [DE] Fed. Rep. of Germany ....... 3900588

[51] Int. Cl.⁵ .......................................... H04R 25/00
[52] U.S. Cl. ..................................... 381/68; 381/68.2; 381/68.6
[58] Field of Search ....................... 381/68, 68.2, 68.6, 381/60; 73/585

[56] References Cited

U.S. PATENT DOCUMENTS

| | | |
|---|---|---|
| 3,531,595 | 9/1970 | Demaree ................................ 179/1 |
| 3,571,529 | 3/1971 | Gharib et al. ....................... 179/107 |
| 3,927,279 | 12/1975 | Nakamura et al. .......... 179/107 FD |
| 3,989,904 | 11/1976 | Rohrer et al. ................ 179/107 FD |
| 4,025,721 | 5/1977 | Graupe et al. ....................... 179/1 P |
| 4,063,410 | 12/1977 | Welling .................................... 58/38 |
| 4,099,163 | 7/1978 | Worley et al. ....................... 348/168 |
| 4,185,168 | 1/1980 | Graupe et al. ....................... 179/1 P |
| 4,187,413 | 2/1980 | Moser .......................... 179/107 FD |
| 4,188,667 | 2/1980 | Graupe et al. ....................... 364/724 |
| 4,189,713 | 2/1980 | Duffy ..................................... 340/168 |
| 4,223,181 | 9/1980 | Simeau .................................... 179/1 |
| 4,228,402 | 10/1980 | Plummer .......................... 179/1 VL |
| 4,259,742 | 3/1981 | Burns et al. ........................... 455/52 |
| 4,297,677 | 10/1981 | Lewis et al. ......................... 340/148 |
| 4,365,633 | 12/1982 | Loughman et al. ......... 128/419 PG |
| 4,396,806 | 8/1983 | Anderson .................... 179/107 FD |
| 4,425,481 | 1/1984 | Mansgold et al. ..................... 381/68 |
| 4,508,940 | 4/1985 | Steeger ......................... 179/107 FD |
| 4,575,586 | 3/1986 | Topholm ........................ 179/107 P |
| 4,633,498 | 12/1986 | Warnke et al. .................... 381/23.1 |
| 4,680,798 | 7/1987 | Neumann ........................... 381/68.4 |
| 4,790,019 | 12/1988 | Hueber ............................... 381/68.4 |
| 4,791,672 | 12/1988 | Nunley et al. ...................... 381/68 |
| 4,845,755 | 7/1989 | Busch et al. ........................ 381/68 |
| 4,918,736 | 4/1990 | Bordewijk ............................ 381/68 |
| 4,947,432 | 8/1990 | Topholm ............................ 381/68.2 |
| 4,972,487 | 11/1990 | Mangold et al. ..................... 381/68 |
| 4,989,251 | 1/1991 | Mangold ............................ 381/68 |
| 4,992,966 | 2/1991 | Widin et al. .......................... 381/68 |
| 5,007,090 | 4/1991 | Bransky et al. .................... 381/68.2 |

FOREIGN PATENT DOCUMENTS 0064042 11/1982 European Pat. Off. ............. 381/68
0176116 4/1986 European Pat. Off. .

(List continued on next page.)

OTHER PUBLICATIONS

Mangold et al., "Wearable Programmable Hearing Aid with Multi-Channel Compression: Successive Adaptation An Interdisciplinary Study Based on Subjective and Objective Evaluation Methods", *Chalmers Tekniske Hogskola,* Swedish Technical University, Gotherberg, Nov. 1980 (with partial translation).

(List continued on next page.)

Primary Examiner—Jin F. Ng
Assistant Examiner—Huyen D. Le
Attorney, Agent, or Firm—Sughrue, Mion, Zinn, Macpeak & Seas

[57] ABSTRACT

A remote-controllable, programmable hearing aid system, including of a hearing aid (2) with incorporated amplifier and with a signal processing circuit whose transmission characteristic can be determined at any time by a set of control parameters, and an external control unit (1) with a transmitter for wireless transmission of control parameters to the hearing aid. A receiving circuit for receiving the control parameters is located in the hearing aid. This system is characterized in that an input device (3) is provided for input of data/information, and a data processing device (4) is provided for derivation of control parameters from the audiometric data/information for transmission from the control unit to the hearing aid.

7 Claims, 2 Drawing Sheets

FOREIGN PATENT DOCUMENTS

| | | | |
|---|---|---|---|
| 0335542 | 10/1989 | European Pat. Off. | 381/68 |
| 3642828 | 8/1987 | Fed. Rep. of Germany | 381/68.2 |
| 52-50646 | 12/1977 | Japan . | |
| 53-75013 | 6/1978 | Japan . | |
| 54-92146 | 6/1979 | Japan . | |
| 8001632 | 8/1980 | PCT Int'l Appl. . | |
| 2006559 | 5/1979 | United Kingdom . | |
| 2016767 | 9/1979 | United Kingdom . | |
| 2091065 | 7/1982 | United Kingdom . | |

OTHER PUBLICATIONS

Mangold, "Programmable Hearing Aid" *Uses of Computers in Aiding the Disabled*, IFIP-IMIA Working Conference, Haifa, Israel, Nov. 3–5, 1981, pp. 135–146.

S. Mangold et al., "Programmable Hearing Aid with Multichannel Compression," Scan Audiol 8: 121–126, 1979.

Widex A8+T and A8+H Hearing Aids Brochure (1977).

Widex Model S20 Hearing Aid Brochure (1980).

*Audiology*, Gunnar Lidén, Sweden (1975), pp. 238–239 and 246–247 (translation attached).

R. P. Lippmann et al., "Study of Multichannel Amplitude Compression and Linear Amplification for Persons with Sensorineural Hearing Loss," Journal of the Acoustic Society of America, vol. 69, No. 2, Feb. 1981, pp. 524–534.

S. G. Knorr, "A Hearing Aid for Subjects with Extreme High-Frequency Losses," IEEE Transactions on Acoustics, Speech and Signal Processing, Dec., 1976, pp. 473–480.

Rihs et al., "Active Filtering—a Step Toward the Programmable Hearing Aid," Hearing Instruments, vol. 33, No. 10, 1982.

Mangold et al., "Multichannel Compression in a Portable Programmable Hearing Aid," Hearing Aid Journal, Apr. 1981, pp. 6, 29–30, 32.

Moser, "Hörgerät mit diskreter Signalverarbetung" (Hearing Aid with Discrete Signal Processing) Zeitschrift für Högeräte-Akustik, Band 17, 1978, Heft 4 (Jul.), pp. 124–135.

Katz et al., "A Portable Tactile Aid for the Deaf using a Z80 Microprocessor Controller," *Proceedings of New England Boerg Conference*, pp. 336–339 (Mar. 22, 1979).

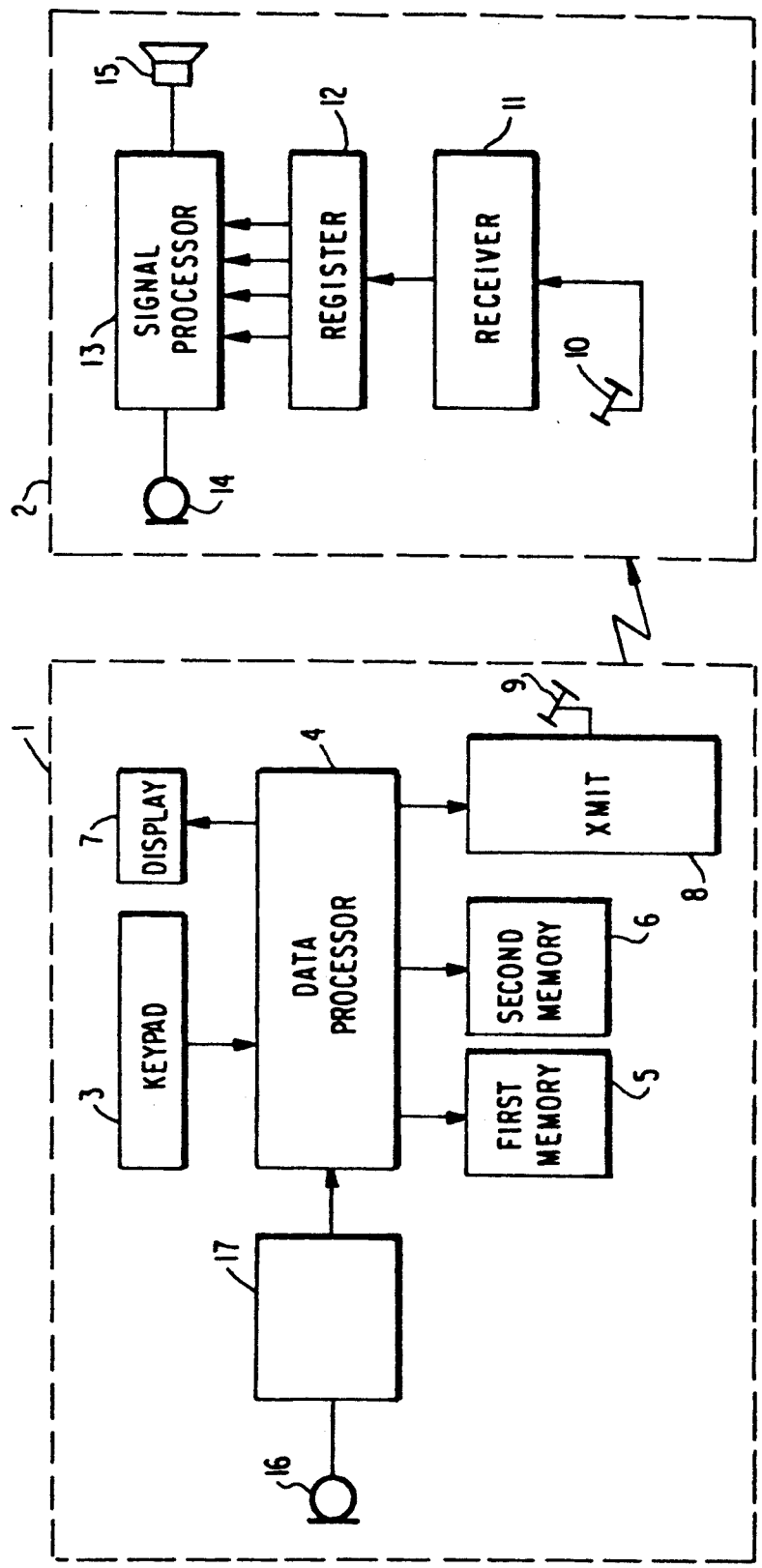

REMOTE-CONTROLLABLE, PROGRAMMABLE, HEARING AID SYSTEM

BACKGROUND OF THE INVENTION

The invention relates to any remote-controllable, programmable, hearing aid system, e.g., as disclosed in U.S. Pat. No. 4,947,432.

In this system, a basic transmission characteristic is permanently set in the actual hearing aid in the individual stages of the transmission channel from the microphone to the earphone. Other transmission characteristics are stored in an external control unit and can be optionally selected by operation of a switch or pushbutton and transmitted to the receiver provided in the hearing aid by means of a transmitter incorporated in the external control unit.

After demodulation and corresponding processing, the signals picked up by the hearing aid serve the purpose of setting a different transmission characteristic of the hearing aid between the microphone and earphone for adaptation to one of several environmental situations digitally stored in an external control unit, for example in the form of control parameters.

SUMMARY OF THE INVENTION

However, this already very good system can be further improved by moving away completely from fixed transmission functions both in the hearing aid itself and in the control unit and thus not just considerably improving the versatility of the device but also decisively simplifying programming.

This is achieved by the invention by means of the characteristics of patent claim 1.

Refer to the other claims for further characteristics of the invention.

BRIEF DESCRIPTION OF THE DRAWINGS

The invention will now be described in conjunction with the accompanying drawings wherein:

FIG. 3 is a block diagram of a further realization form of the invention.

DETAILED DESCRIPTION OF THE INVENTION

Figure 1:
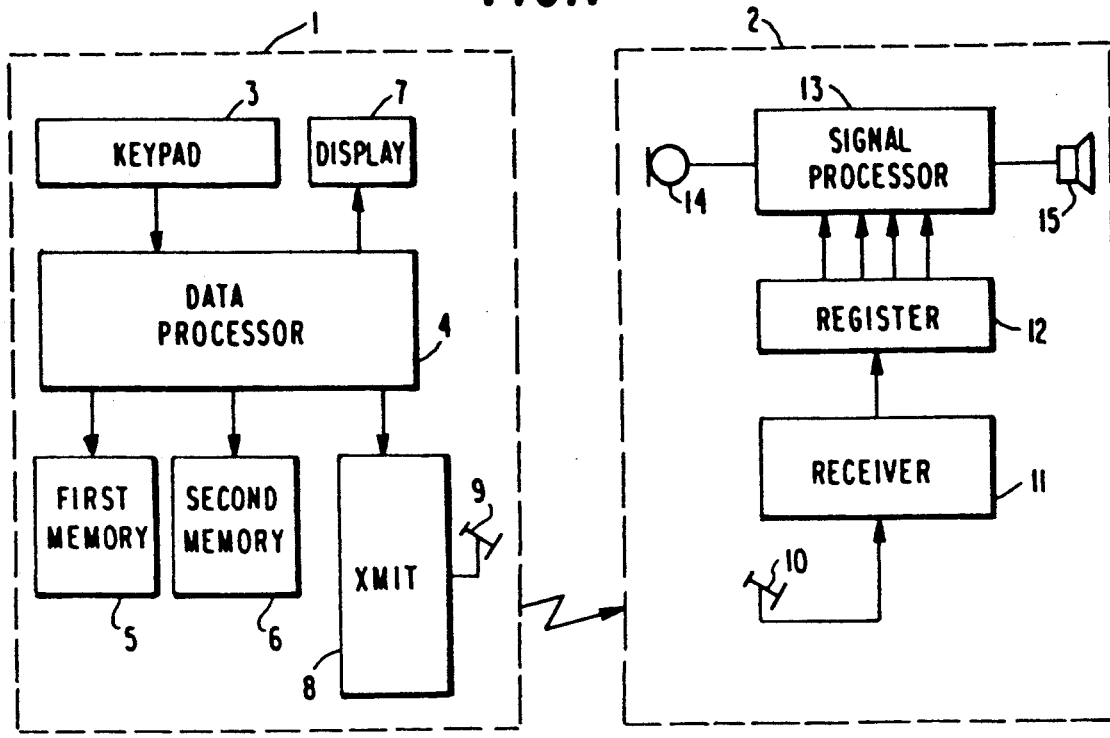
FIG. 1 is a simplified block diagram of the hearing aid in accordance with the invention.

FIG. 1 shows a remote-controllable, programmable hearing aid system which consists of an external control unit 1 and an actual hearing aid 2, whereby the latter may be a device to be worn behind the ear or a device to be worn in the ear, for example.

In-ear devices may also be devices which are worn directly at the concha.

The control unit may possibly have the form of a device shown in U.S. Pat. No. 4,947,432, but may also be a programming device intended for a hearing aid acoustic specialist, this then allowing the control unit to be programmed in accordance with the above patent.

For simplicity's sake, let us take the first example for explanation purposes.

The control unit 1 contains a keypad 3 with a large number of keys or pushbuttons for input of audiometric data/information, data/information related to environmental situations and for calling data/information for a display.

This keypad 3 is connected to a data processor 4, i.e. microprocessor, to which a first memory 5 for audiometry data and a second memory 6 for data describing various environmental situations are connected in turn.

In addition, a display 7, for example in the form of a liquid-crystal display, is connected to the data processor 4. Finally, a transmitter 8 is also connected to the data processor 4, whereby the former is intended for wireless transmission of data/parameters to the actual hearing aid. An antenna 9 is provided on the transmitter for this purpose.

The hearing aid possesses a receiving antenna 10. The signals received there are demodulated in a receiver 11 and output to a control parameter register 12. There, the parameters intended for a specific transmission characteristic are converted from serial form to parallel form and supplied to individual stages of an amplifier and signal processor 13 for the respectively required adjustments of the transmission characteristic between the microphone 14 and earphone 15.

The control unit 1 with its keypad 3 is used, as already mentioned, for input of the audiometric data of a patient. These data relate in each case to the hearing loss at a number of discrete frequencies, i.e. at 125 Hz, 250 Hz, 500 Hz, 1000 Hz, 2000 Hz etc.

Each of these values is entered by means of the keypad 3, whereby the value for each frequency is changed automatically by step-by-step paging, a process which can be followed on the microprocessor-controlled display 7 until the desired input value appears on the display. This value is then recorded as a control parameter and stored in memory 5. This same procedure is followed for the other values until the whole audiogram is stored in memory 5.

The transmission characteristic of the hearing aid can be adjusted for normal operation with the parameter values determined in this way.

It is known that such a basic setting is not suitable for a wide variety of environmental situations. For this reason, the new hearing aid permits calculation or derivation of parameters for various environmental situations in the same way using the keypad 3 in conjunction with the display 7 and data processing device 4 with subsequent storage in memory 6.

If the hearing aid is to be operated with this external control unit, then several program keys must be provided. If one of these program keys is then pressed, the microprocessor calls the corresponding data from memory 6 and modifies the data stored in memory 5 in order to obtain new parameters intended for this particular environmental situation. These are then transmitted to the receiver 11 of the hearing aid by the transmitter 8 and are converted into control parameters for the amplifier and signal processor. The hearing aid is now adjusted for this patient and for a certain environmental situation.

By operation of a different program key, the hearing aid can be adjusted to a different environmental situation. Equally, it is also possible to reset the hearing aid to the basic setting determined by audiometry.

This programming device can also be accommodated in a programming unit intended for a hearing aid acoustic specialist, whereby this can be used for programming a hearing aid as described in the above-mentioned U.S. Pat. No. 4,947,432. In this way, the new hearing aid can also be reprogrammed to the changed audiometric data of the patient at any time. In addition, other data can be entered and stored to replace already stored data for environmental situations. This makes this device extremely versatile.

Figure 2:
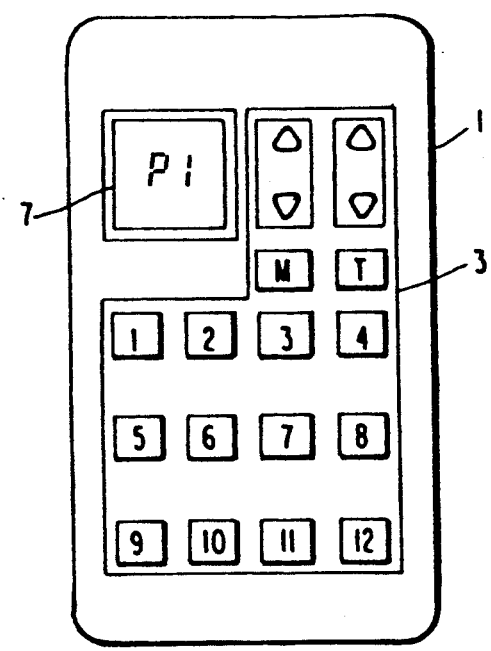
FIG. 2 shows an external control unit.

FIG. 2 shows such an external control unit in schematic form, whereby this may be similar to the control unit in accordance with the above-mentioned patent.

This control unit 1 possesses a display 7, e.g. in the form of a liquid-crystal display, and a keypad 3 on its surface.

The keys marked with arrows on keypad 3 are used for the above-mentioned paging process when entering audiometric data. In this design form, the left switch is used for a hearing aid intended for the left ear and the right switch for a hearing aid intended for the right ear. The key M is used for switching on the microphone in the hearing aid and the key T for switching on a telephone coil. Keys 1 to 4 can be assigned as program keys, e.g., for calling different parameter sets from the parameter memories 5 and/or 6, and serve to initiate transmission of corresponding control parameters to the hearing aid.

The configuration may be realized, for example, such that a group of control parameters which takes into account a certain environmental situation and which is stored in memory 6 can be called to modify the standard parameters stored in parameter memory 5. It is thus possible to take into account several environmental situations.

Here, the parameters of the standard setting from memory 5 are modified by the microprocessor with the parameters from parameter memory 6, for example, and the parameters modified in this way are then transmitted to the hearing aid to set the new transmission characteristic of the hearing aid. In other words, the standard setting is allocated to one of the keys 1 to 4, for the hearing aid itself does not have a permanent transmission characteristic setting, but always only the setting corresponding to one of the program keys.

Since the parameters stored in memories 5 and 6 can be reprogrammed at any time when required by the hearing aid acoustic specialist, this device can be adapted to practically any new situation, something which is true both for the basic setting and for parameters for various environmental situations.

The additional keypad rows shown in FIG. 2 with four additional keys in each case are intended only to symbolically represent the input means for audiometry data and data for specific environmental situations. Allocation of individual keys and their number and layout will naturally be adapted to the respective requirements and this does not form part of the invention.

What is the probably the most elegant variant of the new hearing aid can be realized with an additional microphone 16 incorporated in the external control unit in accordance with FIG. 3. This microphone may be switched on, for example, by one of the four program keys, i.e. program key 4.

This microphone picks up the current environmental situation, e.g. noise in a living room, in a train compartment or tram or reception with many participants, as an audio signal and supplies to this to the analysis and evaluation circuit 17. This circuit analyzes this signal according to its energy content over the whole frequency range in question here and determines a set of control parameters corresponding to the recorded audio signal for transmission to the hearing aid. This is done by means of one or more stored algorithms with the assistance of the microprocessor of the data processing device 4 in conjunction with the control parameters derived from the audiometric data.

It is possible to go one step further and omit the program keys and input keys for environmental situations and the memory for environmental parameters.

In this case, the external control unit is provided with a memory for the control parameters derived from the audiometric data for the basic setting in addition to the input keypad for the audiometric data. All other settings are then determined, collected or derived automatically via the external control unit and the microphone 16 incorporated in this by analysis of the sound pattern or noise pattern by the microprocessor with the assistance of stored algorithms. These settings are then used directly to control the transmission characteristic of the hearing aid.

These algorithms can either be stored in a read-only memory outside or inside the data processing device or they may also be located in a dynamic volatile memory which is either connected to the data processing device or contained in this. In this case, the algorithms can be changed if required.

It is thus ensured that the hearing aid can be used directly for any environmental situation and that it automatically adapts itself to a new listening situation as result of a change to a different environmental situation.

In such a configuration, it is possible to control operation of the new hearing aid completely by means of the display by having all information intended for operator prompting shown on the display.

It has thus been shown that the known hearing aid has been decisively improved by the invention.

What is claimed is:

1. A remote-controllable, programmable hearing air system, comprising an external control unit (1) and a hear air (2), said external control unit includes an input device (3), a display (7) for operator prompting and a transmitter for optional transmission of different groups of control parameters to said hearing air, said hearing aid having a receiving circuit and a signal processing circuit whose transmission characteristic can be optionally adjusted at any time by a set of said control parameters transmitted by said external control unit, wherein said remote control unit contains a first memory (5) for storing audiometric data, a second memory (6) for storing data characterizing different environmental situations, and a data processing device (4) for determination of a set of control parameters from the contents of said first and second memories.

2. A hearing aid system in accordance with claim 1, wherein said data processing device comprises a microprocessor connected to said input device, said display, said first and second memories and said transmitter.

3. A hearing aid system in accordance with claim 1, wherein said external control unit includes a third memory for storing at least one algorithm, and wherein said data processing device determines said set of control parameters in accordance with said algorithm.

4. A hearing aid system in accordance with claim 3, wherein at least one of said first and second memories and the third memory are integrated in the microprocessor.

5. A hearing aid system in accordance with claim 1, wherein said external control unit is equipped with an additional microphone (16) providing an output representing current environmental conditions, characterized in that the data processing device is responsive to said output of said microphone to derive control parameters corresponding to said current environmental conditions for transmission to said hearing aid.

6. A hearing aid in accordance with claim 5, wherein said external control unit further includes an analysis and evaluation circuit (17) for evaluating said current environmental conditions and for providing an output to said data processing device.

7. A hearing aid system in accordance with claim 1, characterized in that the display is provided for display of data/information stored in the storage media of the hearing aid system, for display of data/information which has been processed or derived by said data processing device as well as for display of the information for operator prompting.

* * * * *

UNITED STATES PATENT AND TRADEMARK OFFICE
CERTIFICATE OF CORRECTION

PATENT NO. : 5,202,927
DATED : April 13, 1993
INVENTOR(S) : Tøpholm

It is certified that error appears in the above-indentified patent and that said Letters Patent is hereby corrected as shown below:

Column 4, line 34, delete "hearing air" and insert --hearing aid--.

line 36, delete "hear air" and insert --hearing aid--.

line 39, delete "hearing air" and insert --hearing aid--.

Signed and Sealed this

Fourth Day of January, 1994

Attest:

BRUCE LEHMAN

Attesting Officer        Commissioner of Patents and Trademarks